(12) United States Patent
Gilbert et al.

(10) Patent No.: US 9,084,765 B2
(45) Date of Patent: *Jul. 21, 2015

(54) USE OF AMISULPRIDE AS AN ANTI-EMETIC

(75) Inventors: Julian Clive Gilbert, Cambridgeshire (GB); Robert William Gristwood, Cambridge (GB); Nicola Cooper, Essex (GB); Gabriel Fox, Cambridgeshire (GB)

(73) Assignee: Acacia Pharma Limited, Cambridgeshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/559,168

(22) Filed: Jul. 26, 2012

(65) Prior Publication Data

US 2013/0022688 A1 Jan. 24, 2013

Related U.S. Application Data

(63) Continuation of application No. PCT/GB2011/050472, filed on Mar. 10, 2011.

(30) Foreign Application Priority Data

Mar. 11, 2010 (GB) .................................. 1004020.2

(51) Int. Cl.
| | | |
|---|---|---|
| A61K 31/40 | (2006.01) | |
| A61K 38/00 | (2006.01) | |
| C07K 14/47 | (2006.01) | |
| A61K 33/24 | (2006.01) | |
| A61K 9/00 | (2006.01) | |
| A61K 31/282 | (2006.01) | |
| A61K 31/4178 | (2006.01) | |
| A61K 31/485 | (2006.01) | |
| A61K 47/12 | (2006.01) | |
| A61K 45/06 | (2006.01) | |

(52) U.S. Cl.
CPC ............... *A61K 33/24* (2013.01); *A61K 9/0019* (2013.01); *A61K 31/282* (2013.01); *A61K 31/40* (2013.01); *A61K 31/4178* (2013.01); *A61K 31/485* (2013.01); *A61K 45/06* (2013.01); *A61K 47/12* (2013.01)

(58) Field of Classification Search
USPC .................................. 424/649; 514/166, 408
See application file for complete search history.

(56) References Cited

U.S. PATENT DOCUMENTS

| | | | | |
|---|---|---|---|---|
| 4,294,828 | A * | 10/1981 | Thominet et al. | 514/166 |
| 8,686,019 | B2 * | 4/2014 | Gilbert et al. | 514/408 |
| 2008/0188537 | A1 * | 8/2008 | Azorin | 514/408 |
| 2009/0175939 | A1 | 7/2009 | Bosse et al. | |

FOREIGN PATENT DOCUMENTS

| | | | |
|---|---|---|---|
| DE | 10 2005 013726 A1 | | 9/2006 |
| WO | WO 00/03740 A2 | | 1/2000 |
| WO | WO0003740 | * | 1/2000 |
| WO | WO 0003740 A2 | * | 1/2000 |
| WO | WO 03/053427 A1 | | 7/2003 |
| WO | WO 2006/106358 A2 | | 10/2006 |
| WO | WO 2007/067714 A2 | | 6/2007 |
| WO | WO 2007/093909 A1 | | 8/2007 |
| WO | WO-2007090082 A2 | | 8/2007 |
| WO | WO 2009/126931 A2 | | 10/2009 |

OTHER PUBLICATIONS

Torta, R. et al., Amisulpride in the short-term treatment of depressive and physical symptoms in cancer patients during chemotherapies., Feb. 14, 2007, Support Care Cancer, vol. 15, pp. 539-546.*
Hesketh, P., Chemotherapy-Induced Nausea and Vomiting., Jun. 5, 2008, The New England Journal of Medicine, vol. 358, No. 23, pp. 2482-2494.*
Porreca, F. et al., Nausea and Vomiting Side Effects with Opioid Analgesics During Treatment of Chronic Pain: Mechanisms, Implications, and Management Options., Nov. 4, 2009, Pain Medicine, vol. 10, No. 4, pp. 654-663.*
Pizzo, B.A. et al., Oral cisapride for the control of delayed vomiting following high-dose cisplatin., 1999, Support Care Cancer, vol. 7, No. 1, pp. 44-46.*
McCracken, G. et al., Guideline for the Management of Postoperative Nausea and Vomiting. Jul. 2008, SOGC Clinical Practice Guideline, No. 209, pp. 600-607.*
McCracken et al., Guideline for the Management of Postoperative Nausea and Vomiting, Jul. 2008, SOGC Clinical Practic Guideline, No. 209, pp. 600-607.*
McCracken et al, Guideline for the Management of Postoperative Nausea and Vomiting, 2008, SOGC Clinical Practice Guideline, No. 209, pp. 600-607.*
Torta et al, Amisulpride in the short-term treatment of depressive and physical symptoms in cancer patients during chemotherapies, 2007, Support Care Cancer, 15, pp. 539-546.*
Porreca et al, Nausea and Vomiting Side Effects with Opioid Analgesics during Treatment of Chronic Pain: Mechanisms, Implications, and Management Options, 2009, vol. 10, No. 4, pp. 654-662.*

(Continued)

*Primary Examiner* — Jason Sims
*Assistant Examiner* — Tori M Strong
(74) *Attorney, Agent, or Firm* — Cooley LLP; Ivor R. Elrifi; Heidi A. Erlacher

(57) ABSTRACT

Amisulpride is used in the therapy of nausea, vomiting or retches. The therapy may utilize a novel injectable formulation, in unit dosage form, comprising less than 50 mg amisulpride.

33 Claims, No Drawings

(56) References Cited

OTHER PUBLICATIONS

Pizzo et al, Oral cisapride for the control of delayed vomiting following high-dose cisplatin, 1999, Support Care Cancer, 7, pp. 44-46.*
Torta et al., Amisulpride in the short-term treatment of depressive and physical symptoms in cancer patients during chemotherapies, 2007, Support Care Cancer, 15, pp. 539-546.*
Cook-Sather, S. et al., "Cisapride Does Not Prevent Postoperative Vomiting in Children" *Anesth Analg*, 2002, vol. 94, No. 1, pp. 50-54.
Depoortere, R. et al., "Apomorphine-induced emesis in dogs: Differential sensitivity to established and novel dopamine $D_2/5-HT_{1A}$ antipsychotic compounds" *European Journal of Pharmacology*, Nov. 2008, vol. 597, No. 1-3, pp. 34-38.
Hesketh, P.J., "Chemotherapy-Induced Nausea and Vomiting", *The New England Journal of Medicine*, Jun. 2008, vol. 358, No. 23, pp. 2482-2494.
Jordan, K. et al., "Neue antiemetische Strategien a nicht nur in der Onkologie" *Der Internist*, May 2009, vol. 50, No. 7. pp. 887-894. (English Abstract on p. 889).
Pizzo, B.A. et al. "Oral cisapride for the control of delayed vomiting following high-dose cisplatin" *Supportive Care in Cancer*, 1999, vol. 7, No. 1, pp. 44-46.
Puech, A.J., et al. "Pharmacological Classification of Benzamides" Jan. 1, 1984, pp. 139-143.
Torta, R. et al. "Amisulpride in the short-term treatment of depressive and physical symptoms in cancer patients during chemotherapies" *Supportive Care in Cancer*, Feb. 2007, vol. 15. No. 5, pp. 539-546.
Porreca, Frank and Michael H. Ossipov "Nausea and Vomiting Side Effects with Opioid Analgesics During Treatment of Chronic Pain: Mechanisms, Implications, and Mangement Options," *Pain Medicine* 10(4):654-663, 2009.
Hesketh. "Defining the Emetogenicity of Cancer Chemotherapy Regimens: Relevance to Clinival Practice." *Oncologist*. 4(1999):191-196.
Kranke et al. "Intravenous Buspirone for the Prevention of Postoperative Nausea and Vomiting." *Eur. J. Clin. Pharmacol.* 68(2012):1465-1472.
Hirokawa et al. "Synthesis and Structure-Affinity Relationships of Novel N-(1-Ethyl-4-methylhexahydro-1, 4-diazepin-6-yl) pyridine-3-carboxamides with Potent Serotonin 5-HT3 and Dopamine D2 Receptor Antagonistic Activity", Journal of Medicinal Chemistry, American Chemical Society, US, vol. 46, No. 5, Jan. 2, 2003, pp. 702-715.
Magnani M., "Amisulpride Pharmacological and biochemical aspects", Farmacia E Clinica, IT, vol. 33, No. 3, Jan. 1, 1994, pp. 91-97.
Chen Graham et al., "The Influence of Diphenhydramine•HC1 (Benadryl) on Apomorphine-Induced Emesis in Dogs", Journal of Pharmacology and Experimental Therapeutics, Mar. 1950 98:245-250.
Makita, K., Practical Anesthesia Series "Countermeasure to PONV and Anesthesia," Anet. (quarterly journal), Maruishi Pharmaceutical, 2004, pp. 18-24, vol. 8, No. 2 (No English translation available).
Minami, M. et al., "Role of serotonin in emesis," Folia Pharmacol., 1996, pp. 233-242, vol. 108 (No English translation available).
Takei, D. et al., "Drug Therapy for Nausea and Vomiting," J. Pharm. Palliat. Care Sci., 2009, pp. 111-117, vol. 2 (No English translation available).
Murakuni, H., Palliative Medicine Lectures ABC, "Mechanism of action of morphine in nausea/vomiting and countermeasures," Palliative Medicine, 2001, pp. 72-78, vol. 3, No. 1 (No English translation available).

\* cited by examiner

USE OF AMISULPRIDE AS AN ANTI-EMETIC

CROSS REFERENCE TO A RELATED APPLICATION

This application is a continuation application of International Application Number PCT/GB2011/050472, filed Mar. 10, 2011; which claims priority to Great Britain Application No. 1004020.2, filed Mar. 11, 2010; which are incorporated herein by reference in their entirety.

FIELD OF THE INVENTION

This invention relates to the use of amisulpride in the therapy of nausea, vomiting and retching.

BACKGROUND OF THE INVENTION

Emesis is the act of vomiting and can be described as the forceful expulsion of gastrointestinal contents through the mouth brought about by the descent of the diaphragm and powerful contractions of the abdominal muscles. Emesis is usually, but not always, preceded by nausea. Retching (or dry heaves) involves the same physiological mechanisms as vomiting, but occurs against a closed glottis. Nausea may be defined as a desire to vomit but which is not associated with expulsive muscular movement.

Vomiting, nausea, retching or any combination (hereinafter referred to as "the symptoms") can be caused by a number of factors including anaesthetics, radiation, cancer chemotherapeutic agents, toxic agents, medicines, for example serotonin reuptake inhibitors, analgesics such as morphine, antibiotics, pregnancy and motion. Conditions which are associated with vertigo, for example Meniere's disease, can also cause the symptoms. Headache, caused by for example migraine, increased intracranial pressure or cerebral vascular haemorrhage can also result in the symptoms. Other maladies associated with the symptoms include cholecystitis, choledocholithiasis, intestinal obstruction, acute gastroenteritis, perforated viscus, dyspepsia resulting from, for example, gastroesophogeal reflux disease, peptic ulcer disease, gastroparesis, gastric or oesophageal neoplasms, infiltrive gastric disorders (e.g. Menetrier's syndrome, Crohn's disease, eosinophilic gastroenteritis, sarcoidosis and amyloidosis), gastric infections, parasites, chronic gastric volvulus, chronic intestinal ischaemia, altered gastric motility disorders and/or food intolerance or Zollinger-Ellson syndrome. In some cases of the symptoms, no etiology can be determined, as for example in Cyclic Vomiting Syndrome.

The symptoms may be defined as acute when they are present for less than a week. The causes of the symptoms of short duration can be separable from etiologies leading to more chronic symptoms. The symptoms may be defined as chronic when they are present for over a week; these can be continuous or intermittent, and last for months or years.

Two areas of particular clinical relevance are nausea and vomiting resulting from surgical procedures (post-operative nausea and vomiting, or PONV) or chemotherapeutic agents and radiation therapy (chemotherapy-induced nausea and vomiting, or CINV). The symptoms caused by chemotherapeutic agents can be so severe that the patient refuses further treatment. Three types of emesis are associated with the use of chemotherapeutic agents, i.e. acute emesis, delayed emesis and anticipatory emesis.

PONV is a significant issue for patients and healthcare providers. It is rated second only to pain as the complication most feared by patients, and contributes significantly to anxiety and patient distress. Vomiting can have an adverse impact on surgical wound sites, especially upper GI tract surgery.

Risk factors for PONV include type of surgery, gender (women are more prone than men to PONV), smoking history, prior history of PONV or motion sickness, length of surgery, use of volatile anaesthetics and opioid analgesic usage. Certain operations seem to be particularly associated with PONV, including procedures on the eyes and ears, laparoscopic cholecystectomy and hysterectomy, breast surgery and major abdominal and gynaecological surgery.

PONV is typically treated using a dopamine D2 antagonist such as droperidol. This drug was given a black box warning by the FDA in 2001 on the basis of cardiotoxicity, believed to be related to a propensity of the drug to block HERG channels and cause QT prolongation.

Amisulpride, an atypical antipsychotic D2 antagonist, has beneficial actions in schizophrenic patients. For patients characterised by predominant negative symptoms, oral doses of 50-300 mg/day are recommended. It is reported in the UKPAR (Special Warnings and Precautions for Use) that amisulpride induces a dose dependent prolongation of the QT interval.

Amisulpride is marketed as Solian, a solution for intramuscular administration, comprising water, hydrochloric acid, sodium chloride and amisulpride. An ampoule contains amisulpride at 200 mg/4 ml solution.

U.S. Pat. No. 4,294,828 discloses amisulpride and related compounds having anti-apomorphine and anti-serotonin activity. Amisulpride is reported to inhibit apomorphine-induced vomiting in the dog, thereby confirming that amisulpride is a functional D2 antagonist. It is suggested that the compounds should be administered at doses of 50-750 mg/day, e.g. 200 mg/day.

SUMMARY OF THE INVENTION

The present invention relates to the use in man of amisulpride for the therapy (including treatment and prophylaxis or preventative therapy) of nausea, vomiting or retching. The condition may have any cause, e.g. motion sickness, but amisulpride may be particularly useful in therapy of PONV or in patients receiving cancer chemotherapy or radiotherapy.

As will be evident from the data presented below, amisulpride is effective as an anti-emetic agent, even when the subject is receiving morphine or cisplatin, both agents whose emetic effect is strong and difficult to alleviate. Surprisingly, it is also effective at a dose well below any that has previously been proposed for this drug. Therefore, although side-effects are not as much of a concern when using amisulpride as in the case of some other anti-emetic drugs, such effects can be minimised or avoided.

Another aspect of the invention is a product comprising amisulpride and an emetogenic agent, as a combined preparation for separate, simultaneous or sequential use in the therapy of a condition as defined herein.

A further aspect of the present invention is a buffered composition suitable for injection. Yet another aspect of the present invention is a unit dosage for injection comprising less than 50 mg amisulpride.

DESCRIPTION OF THE INVENTION

Amisulpride has a single chiral centre and 2 enantiomers exist, i.e. (S-)-amisulpride and (R+)-amisulpride. Substantially pure enantiomer or non-racemic mixtures may be used, but it may be preferred to use racemate or (S-)-amisulpride.

For the purpose of the present invention, amisulpride may be administered at dosages which are not associated with adverse cardiovascular events. It is preferably administered by the intravenous, intramuscular, subcutaneous or oral route for the treatment of PONV, whilst for the treatment of CINV additional routes include sublingual, rectal, intranasal, topically applied directly to the skin, buccal or pulmonary inhaled.

A typical dosage, e.g. for intravenous administration, is from 1 to 48 mg, e.g. up to 40 mg, preferably 1 to 35 mg or, depending on the circumstances, 5 to 35 mg. Human doses of 2.5 to 20 mg may be effective. The drug may be given once, twice or more often each day, particularly for CINV. A single dosage may be sufficient for PONV. It will be understood, however, that the specific dose level for any particular patient will depend upon a variety of factors including the age, body weight, general health, sex, diet, time of administration, drug combination and the severity of the particular condition undergoing therapy.

For intravenous injection, the amisulpride may be in the form of a salt, hydrate or solvate. Salts include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

A pharmaceutical composition containing the active ingredient may be in any suitable form, for example aqueous or non-aqueous solutions or suspensions, dispersible powders or granules, transdermal or transmucosal patches, creams, ointments or emulsions.

The pharmaceutical compositions may be in the form of a sterile injectable aqueous or non-aqueous (e.g. oleaginous) solution or suspension. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, phosphate buffer solution, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables. Suspensions may be formulated according to the known art using those suitable dispersing or wetting agents and suspending agents which have been mentioned elsewhere.

Aqueous suspensions contain the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Non-aqueous (i.e. oily) suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. These compositions may be preserved by the addition of an anti-oxidant such as ascorbic acid.

Compositions for injection are typically aqueous, and comprise a buffer, e.g. citrate buffer. No other ingredients may be required. The pH of such a composition may be, for example from 4 to 7, e.g. 5.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

The active agent may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical delivery, transdermal and transmucosal patches, creams, ointments, jellies, solutions or suspensions may be employed. For sub-lingual delivery, fast dissolving tablet formulations may be used, as well as a number of the presentations described above. For oral administration, amisulpride may be administered as tablets, capsules or liquids.

It may be advantageous to co-administer amisulpride with other classes of drug which can add additional benefits of efficacy and/or, by titrating dosages downwards, result in fewer side-effects. These include, but are not limited to, antihistamines, 5-HT3 antagonists including granisetron, ondansetron, palonosetron, dolasetron, and tropisetron, dexamethasone, aprepitant and other neurokinin-1 receptor antagonists and drugs such as nabilone.

It may also be advantageous to co-administer amisulpride with drugs which are associated with emesis in man, for example certain opioids including morphine. Amisulpride, at an appropriate concentration determined by one of skill, can be formulated with the drug in question, for example morphine, in a dosing system such as an infusion bag or other appropriate dosage form.

By way of example, amisulpride and an emetogenic agent may be administered to a subject in combination, simultaneously or sequentially. For example, amisulpride is given before treatment with, say, morphine or a chemotherapeutic agent such as cisplatin. As indicated above, the route of administration may depend on the condition being treated.

As indicated above, there are various causes of emesis. Examples of conditions that may be treated by the use of amisulpride include anaesthetics, radiation, cancer chemotherapeutic agents, toxic agents, medicines, for example serotonin reuptake inhibitors, analgesics such as morphine, antibiotics, pregnancy, motion, conditions which are associated with vertigo, for example Meniere's disease, headache, caused by for example migraine, increased intracranial pressure or cerebral vascular haemorrhage, cholecystitis, choledocholithiasis, intestinal obstruction, acute gastroenteritis, perforated viscus, dyspepsia resulting from, for example, gastroesophogeal reflux disease, peptic ulcer disease, gastroparesis, gastric or oesophageal neoplasms, infiltrive gastric disorders (e.g. Menetrier's syndrome, Crohn's disease, eosinophilic gastroenteritis, sarcoidosis and amyloidosis), gastric infections, parasites, chronic gastric volvulus, chronic intestinal ischaemia, altered gastric motility disorders and/or food intolerance and Zollinger-Ellson syndrome.

The following studies provide evidence on which the invention is based. The preclinical evidence for efficacy against vomiting in PONV and CINV involves studies in ferrets, whilst efficacy against nausea can be demonstrated in patients receiving a general anaesthetic procedure.

Study 1

Amisulpride, white powder, was dissolved in dimethylsulfoxide and then diluted in physiological saline.

For vehicle control, physiological saline was used for s,c, administration (apomorphine experiments) and 8.3% DMSO in physiological saline was used for i.v. administration (morphine, cisplatin).

Droperidol was dissolved in DMSO then diluted in lactic acid in physiological saline, to a final DMSO concentration of 7.5%.

Apomorphine hydrochloride hemihydrates, white powder, was dissolved in physiological saline.

Morphine hydrochloride, white powder, was dissolved in physiological saline.

Cisplatinum II diamine dichloride, yellow powder, was dispersed in 0.2% hydroxymethylcellulose in physiological saline.

The method used to test antiemetic activity preclinically follows that described by Gardner et al. (*Brit. J. Pharmacol.*, 116: 3158-3163, 1995) and uses ferrets.

Sixty minutes before administration of the test substance, ferrets are placed in individual stainless steel cages (40×50× 34 cm) with a grid floor. Then, the animals are challenged with apomorphine (0.25 mg/kg s.c.), morphine (0.4 mg/kg i.p.) or cisplatin (10 mg/kg i.p.) and immediately observed over at least a 2-hour period. Parameters recorded include: number of ferrets showing retches and vomits; latency to first retching; latency to first vomiting; number of retches; vomiting (number of vomits); number of emesis periods and mean duration of emesis periods. Retching is defined as a rhythmic respiratory movement against a closed glottis, while vomiting is defined as a forced expulsion of upper gastrointestinal contents.

Where apomorphine is used as the emetogen, amisulpride (or vehicle) was administered subcutaneously (s.c. 30 minutes before administration of apomorphine). Animals (6 per group) were treated with vehicle or amisulpride at 1, 10, or 100 µg/kg given sub-cutaneously. The observation period was 2 hours after apomorphine administration.

Where morphine is used as the emetogen, amisulpride (n=6 per group) or vehicle (n=6) is administered intravenously 5 minutes before the administration of morphine. The observation period is 2 hours after administration of the morphine.

Where cisplatin is used as the emetogen, amisulpride (n=6 per group) or vehicle (n=6) is administered intravenously at least 5 minutes before the administration of cisplatin. The observation period is up to 72 hours, which allows effects on early and late phase emesis to be observed.

Apomorphine in the vehicle control group induced emesis in the ferrets over the 2 hour observation period (14.8±4.8 retches, 1.0±0.5 vomits, 3.3±0.9 emesis periods). Retches and vomits occurred 319±53 and 621±308 seconds after administration respectively. Amisulpride given at 1 µg/kg, 30 minutes before apomorphine, decreased the emetic effects of apomorphine as compared with the vehicle control group (6.0±2.2 retches, 0±0 vomits and 1.5±0.6 emesis periods). Amisulpride at 10 and 100 µg/kg totally inhibited the apomorphine emesis. This demonstrates that, as might be expected, amisulpride blocks dopamine D2 receptors.

Morphine in the vehicle control group induces emesis in the ferrets over the 2 hour observation period. Amisulpride reduces the emetic effects induced by morphine, in dose-dependent manner, as compared with the vehicle control group. The ED50 for amisulpride against morphine emesis is calculated. These data indicate that amisulpride has efficacy against morphine-induced emesis and that is effective when administered via the intravenous route.

More specifically, morphine in the control group induced the occurrence of retches and vomits in 6 (retches) and 4 (vomits) of 6 animals, the mean (±s.e.m.) values were 33.8±4.7 retches, 1.8±0.7 vomits and 7.5±1.5 emesis periods. Retches and vomits occurred after 213±24 and 374±64 seconds respectively. Amisulpride was given at 3, 6 and 12 mg/kg before morphine. Amisulpride at 3 mg/kg produced small decreases in retches to 28.7±7.1 and emesis periods to 5.2±1.4 and abolished the incidence of vomits. Amisulpride given at 6 mg/kg decreased the incidence of all 3 parameters, retches to 17.8±6.8 (approximately a 50% decrease), vomits to 0.5±0.3 (a 72% decrease) and emesis periods to 3.3±1.1 (a 56% decrease). The data from the first 2 dose levels demonstrate a dose related reduction in emesis with amisulpride. Amisulpride given at 12 mg/kg had no effect on retches 31.7±11.2, but still produced a reduction in vomits to 0.8±0.4 and slight reduction in emesis periods to 5.7±1.5.

These data demonstrate that amisulpride blocks morphine-induced emesis, and also that the drug may be less effective at higher dosages. It is reasonable to deduce that a dose of less than 50 mg will be effective in a human subject.

Cisplatin in the vehicle control group induces emesis over the 72 hour period. Amisulpride reduces the emetic effects of cisplatin, in dose-dependent manner, as compared with the vehicle control group, having an effect on both early and late stages.

More specifically, data are reported from an experiment in which the observation period was 3 hours following cisplatin challenge. Cisplatin induced the occurrence of retches and vomits in 7 and 5 of 9 animals tested respectively. The mean incidences were 79.8±22.2 retches, 3.0±1.1 vomits and 10.7±2.8 emetic periods. Retches and vomits occurred after 85 minutes 6 seconds±7 minutes 53 seconds and 86 minutes 39 seconds±10 minutes 28 seconds respectively amisulpride was given at 0.2, 0.6, 2 and 6 mg/kg. At 0.2 mg/kg the incidence of retches was 23.3±10.8 (a 71% decrease in mean value), of vomits 0.2±0.2 (a 93% decrease) and emesis periods 3.7±2.0 (a 65% decrease). At 0.6 mg/kg the incidence of retches was 62.5±59.0, vomits 1.3±1.1 and emesis periods 3.7±1.3. It was noted in this group that one animal had an early, exaggerated response to cisplatin. At 2.0 mg/kg the incidence of retches was 3.3±2.5, vomits 0.2±0.2 and emesis periods 0.5±0.3. It is clear that amisulpride at 0.6 mg/kg (with one animal excluded), and 2 mg/kg is better than droperidol at 3 mg/kg. At 6 mg/kg the incidences were 11.7±3.8 retches, 1.2±1.0 vomits and 3.7±1.3 emesis periods.

These data demonstrate that amisulpride blocks cisplatin-induced emesis, and also indicate that the drug may be less effective at higher dosages. Again, it is reasonable to deduce that a dose of less than 50 mg will be effective in a human subject.

As indicated above, droperidol is a known agent for the treatment of PONV. In a comparative experiment, droperidol was given 5 minutes before cisplatin (using the methods described above) in 3 animals and it was found that, based on the incidence of nausea and vomiting, amisulpride at 0.6 mg/kg (with one animal which had the exaggerated response excluded) and 2 mg/kg is more effective than droperidol at 3 mg/kg.

Study 2

A formulation of the invention was prepared, suitable for intravenous administration. It is a 2.5 mg/ml citrate-buffered solution (nominal pH 5.0) of amisulpride. The composition is given below.

| Component | % w/v | Quantity (g) per vial (10 mL fill) |
|---|---|---|
| Amisulpride | 0.25 | 0.025 |
| Citric acid monohydrate | 0.935 | 0.0935 |
| Trisodium citrate dihydrate | 1.632 | 0.1632 |
| Sodium chloride | 0.18 | 0.018 |
| Hydrochloric acid dilute | qs | qs |
| Sodium hydroxide | qs | qs |
| Water for injection | To 100 | To 10 mL |

The effects of amisulpride are studied in patients undergoing routine surgery in a randomised, controlled, open-label phase IIa study of efficacy of a single dose as prophylaxis of post-operative nausea and vomiting. The primary endpoint is the incidence of nausea and vomiting in the 24-hour period post-operation. The drug is administered at the time of the operation. The secondary endpoints are the nausea and vomiting rates and severity (measured separately) over 0-2 hours, 2-6 hours and 6-24 hours post-operation. In addition, the use of rescue medication and safety/adverse events are recorded. The data demonstrate the effect of amisulpride against the nausea as well as the vomiting and retching associated with PONV.

We claim:

1. A method for the prevention and/or treatment of post-operative nausea and vomiting, wherein said method comprises administering amisulpride racemate at a dose of 2.5 mg to 20 mg to a subject of a surgical procedure and in need of such prevention and/or treatment.

2. The method according to claim 1, wherein the subject is also administered an emetogenic agent.

3. The method according to claim 2, wherein the emetogenic agent is an opiate.

4. The method according to claim 2, wherein the emetogenic agent is morphine.

5. The method according to claim 1, wherein the amisulpride is administered by intravenous injection.

6. The method according to claim 1, wherein the amisulpride is administered by intramuscular injection.

7. The method according to claim 1, wherein the amisulpride is administered by subcutaneous injection.

8. The method according to claim 1, wherein the subject is a human.

9. The method according to claim 1, wherein the amisulpride is in the form of an acceptable pharmaceutical salt.

10. The method according to claim 1, wherein the amisulpride is administered in combination with another anti-emetic drug.

11. The method according to claim 10, wherein the another anti-emetic drug is a 5HT3 antagonist.

12. The method according to claim 11, wherein the 5HT3 antagonist is ondansetron.

13. The method according to claim 1, wherein the amisulpride is administered at a dose of 2.5 mg.

14. The method according to claim 1, wherein the amisulpride is administered at a dose of 5 mg.

15. The method according to claim 1, wherein the amisulpride is administered at a dose of 20 mg.

16. The method according to claim 1, wherein the amisulpride is administered orally.

17. The method according to claim 1, wherein the subject has received an anesthetic.

18. The method according to claim 1, wherein the surgical procedure is chosen from procedures of the eye or ear, laparoscopic cholecystectomy, hysterectomy, breast surgery, abdominal surgery, and gynecological surgery.

19. A method for the prevention and/or treatment of post-operative nausea and vomiting, wherein said method comprises administering amisulpride racemate at a dose of 1 mg to 20 mg to a subject of a surgical procedure and in need of such prevention and/or treatment.

20. The method according to claim 19, wherein the subject is also administered an emetogenic agent.

21. The method according to claim 20, wherein the emetogenic agent is an opiate.

22. The method according to claim 20, wherein the emetogenic agent is morphine.

23. The method according to claim 19, wherein the amisulpride is administered by intravenous injection.

24. The method according to claim 19, wherein the amisulpride is administered by intramuscular injection.

25. The method according to claim 19, wherein the amisulpride is administered by subcutaneous injection.

26. The method according to claim 19, wherein the subject is a human.

27. The method according to claim 19, wherein the amisulpride is in the form of an acceptable pharmaceutical salt.

28. The method according to claim 19, wherein the amisulpride is administered in combination with another anti-emetic drug.

29. The method according to claim 28, wherein the another anti-emetic drug is a 5HT3 antagonist.

30. The method according to claim 29, wherein the 5HT3 antagonist is ondansetron.

31. The method according to claim 19, wherein the amisulpride is administered orally.

32. The method according to claim 19, wherein the subject has received an anesthetic.

33. The method according to claim 19, wherein the surgical procedure is chosen from procedures of the eye or ear, laparoscopic cholecystectomy, hysterectomy, breast surgery, abdominal surgery, and gynecological surgery.

* * * * *